United States Patent [19]

Hemmerling et al.

[11] Patent Number: 4,876,028
[45] Date of Patent: Oct. 24, 1989

[54] CHIRAL ARYL-2,3-EPOXYALKYL-ETHERS AND THE CORRESPONDING THIO COMPOUNDS THEREOF, AND THE USE THEREOF AS DOPES IN LIQUID-CRYSTAL PHASES

[75] Inventors: Wolfgang Hemmerling, Sulzbach; Hans-Rolf Dübal, Hofheim am Taunus; Ingrid Müller, Hofheim am Taunus; Dieter Ohlendorf, Liederbach; Rainer Wingen, Hattersheim am Main, all of Fed. Rep. of Germany

[73] Assignee: Hoechst Aktiengesellschaft, Frankfurt am Main, Fed. Rep. of Germany

[21] Appl. No.: 104,350

[22] Filed: Oct. 2, 1987

[30] Foreign Application Priority Data

Oct. 6, 1986 [DE] Fed. Rep. of Germany ....... 3633968

[51] Int. Cl.$^4$ ................. C07D 239/02; C07D 241/00; C09K 19/34; G02F 1/13
[52] U.S. Cl. ............................. 252/299.61; 544/238; 544/335; 544/336; 544/359; 350/350 R; 350/350 S; 350/346; 252/299.01
[58] Field of Search ............... 544/335, 238, 336, 359; 252/299.61

[56] References Cited

U.S. PATENT DOCUMENTS

4,656,290 4/1987 Kaldor et al. ................. 544/238

FOREIGN PATENT DOCUMENTS

1291574 12/1986 Japan ................... 544/335

Primary Examiner—Mary C. Lee
Assistant Examiner—J. Richter
Attorney, Agent, or Firm—Curtis, Morris & Safford

[57] ABSTRACT

The novel compounds are aryl-2,3-epoxyalkyl ethers or thioethers or the corresponding thiirane compounds having a mesogenic aromatic component and a chiral component having a three-membered heterocyclic ring, wherein, in the general formula (1),

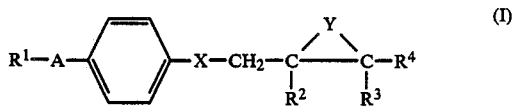

the symbols have the following meaning:
$R^1$=straight-chain or branched ($C_1$–$C_{12}$) alkyl, where one or two non-neighboring $CH_2$ groups may be replaced by O or S atoms.
A=diazine-2,5-diyl or diazine-3,6-diyl,
X and Y=O and/or S, and
$R^2$, $R^3$ and $R^4$, independently of one another=H, straight-chain ($C_1$–$C_{10}$) alkyl or branched ($C_3$–$C_{10}$) alkyl, where $R^2$, $R^3$ and $R^4$ are not simultaneously H.

The compounds are preferably employed in tilted smectic liquid-crystal phases which they convert into ferroelectric liquid-crystal phases; they have high values for spontaneous polarization or they induce high values for spontaneous polarization.

10 Claims, No Drawings

CHIRAL ARYL-2,3-EPOXYALKYL-ETHERS AND THE CORRESPONDING THIO COMPOUNDS THEREOF, AND THE USE THEREOF AS DOPES IN LIQUID-CRYSTAL PHASES

Especially in the last decade, liquid crystals have become involved in a very wide variety of industrial areas in which electro-optical and display device properties are in demand (for example in watch, calculator and typewriter displays). These display devices are based on dielectric alignment effects in the nematic, cholesteric and/or smectic phases of liquid-crystalline compounds, the longitudinal molecular axes of the compounds adopting a preferred alignment—caused by dielectric anisotropy—when an electric field is applied. The customary switching times in these display devices are rather too long for many other potential areas of application of liquid crystals, which are, per se, very promising chemical compounds for technology as a consequence of their unique properties. This disadvantage becomes particularly noticeable when—which is necessarily the case in relatively large display element areas—it is necessary to address a large number of image points, which means that the production costs of these instruments which contain relatively large areas, such as video equipment, oscillographs or TV, radar, EDP or word processor screens, would be too high.

Besides nematic and cholesteric liquid crystals, tilted smectic liquid-crystal phases have also become increasingly important in recent years. If suitable dopes which exhibit so-called spontaneous polarization ($P_s$) or which induce this in the liquid-crystal phase are added to such tilted smectic phases, in particular smectic C($S_c$ or SmC) phases, the phases can be converted into a ferroelectric liquid-crystal phase (specification of $P_s$ in $nC.cm^{-2}$). In this respect see, for example, Lagerwall et al. in the article "Ferroelectric Liquid Crystals for Displays", SID Symposium, October Meeting, 1985, San Diego (USA). Compared to conventional TN ("twisted nematic") cells, these ferroelectric liquid-crystal phases have switching times which are quicker by a factor of about 1000, so that they are good potential candidates for the abovementioned areas of application (for example via matrix addressing), also as a consequence of other positive properties, such as possible bistable switching.

At the 11th International Liquid-crystal Conference (June 30 to July 4 1986) in Berkeley, USA, ferroelectric liquid cyrstals were introduced by D. M. Walba which contain 2,3-epoxy alkyl side chains and have the following general formula:

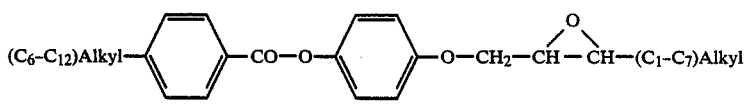

The compound having a $C_{10}$-alkyl or $C_3$-alkyl radical has a SmC* phase between 75° C. and 80° C.; the switching time (75° C., 15 V/μm) is 14 μsec, and the value for spontaneous polarization $P_s$ is 45 $nC/cm^2$.

The object of the present invention is to demonstrate compounds which along with high values for inherent spontaneous polarization $P_s$ or spontaneous polarization induced in liquid-crystal phases, have structural elements which also make them "compatible" (ie. miscible) in liquid-crystal systems, since, inter alia, the mesogenic part of the molecules is often responsible for good "compatibility" with the other mixture components in liquid-crystal systems; these compounds need not necessarily be liquid crystalline themselves, and in particular need not necessarily have a SmC phase.

The invention proceeds from known chiral compounds having a mesogenic aromatic component and a chiral component having a three-membered heterocyclic ring. The compounds according to the invention are then those wherein, in the general formula (I),

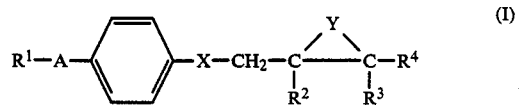

the symbols have the following meaning:
$R^1$=straight-chain or branched ($C_1$-$C_{12}$) alkyl, where one or two non-neighbouring $CH_2$ groups may be replaced by O or S atoms and,
A=diazine-2,5-diyl or diazine-3,6-diyl,
X and Y=O and/or S, and
$R^2$, $R^3$ and $R^4$, independently of one another=H, straight-chain ($C_1$-$C_{10}$) alkyl or branched ($C_3$-$C_{10}$) alkyl, where $R^2$, $R^3$ and $R^4$ are not simultaneously H.

In these compounds, the nitrogen atoms in the diazine ring system may be located in the 1,3- or 1,2-position (pyrimidines or pyridazines respectively), where, in the preferred 1,3-position, the nitrogen atoms may be located on the side of the ring system facing the $R^1$ radical or on the side facing the phenyl ring.

Preferred compounds of the general formula (I) are those in which the symbols have the following meaning: $R^1$=straight-chain ($C_5$-$C_{11}$) alkyl, where a $CH_2$ group may be replaced by an O or S atom, X and Y=O, $R^2$ and $R^3$=H and $R^4$=straight-chain or branched ($C_3$-$C_7$)alkyl.

The compounds of the general formula (I) can be prepared, for example, by reacting phenols or thiophenols of the general formula (II), (III) or (IV) with oxiranes or thiiranes of the general formula (V); in which Z is H or represents a nucleofugic group:

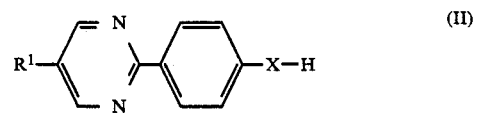

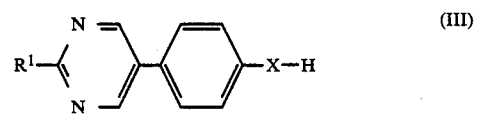

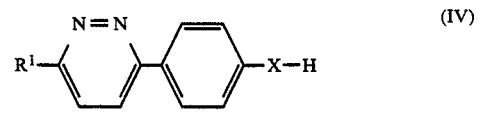

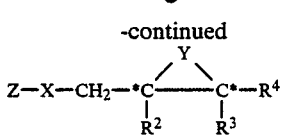

The mesogenic phenols or thiophenols of the general formula (II), (III) or (IV) can be linked to the chiral oxiranes or thiiranes of the general formula (V) in a fashion which is known per se, for example by reacting (II), (III) or (IV) with epoxyalcohols (Y=O,X=O and Z=H) with the aid of diethyl azodicarboxylate and triphenyl phosphine, as described by Mitsonobu, "The Use of Diethyl Azodicarboxylate and Triphenyl Phosphine in Synthesis and Transformation of Natural Products" in Synthesis 1981, pp.1–28. It is also possible to provide the epoxyalcohols with a nucleofugic group Z such that the reaction with alkaline metal or alkaline-earth metal salts of the compound (II), (III) or (IV) leads to formation of the desired ethers of the general formula (I) (where X=O). As such nucleofugic (leaving) groups, tosylates, brosylates, mesylates or triflates, inter alia, are known to those skilled in the art, and can be prepared in a fashion which is known per se, for example from alcohols and the respective acyl chlorides. Corresponding possible reactions also apply to the thiirane compounds.

The educts are compounds which are known from the literature. For example, the compounds (II) where X=O can be prepared by condensation of substituted benzamides with 2-alkylmalonates, conversion of the dihydroxypyrimidines produced into dichloropyrimidines, and subsequent hydrogenolysis (see DE-C 2,257 588). The compounds (III) where X=O are prepared, for example, by condensation of appropriately substituted 2-aryl-3-(methylthio)acroleins with suitable amidines [see Kano et al., "A New and Facile Synthesis of 5-arylpyrimidines and 4-Arylpyrazoles" in Heterocycles, Vol. 19, No. 6, 1079 to 1082 (1982)]. From the phenols, the corresponding thiophenols are obtained by known methods [for example Newman et al., "The Conversion of Phenols to Thiophenols via Dialkylcarbamates" in J. Org. Chem., 31 pp. 3980–3984 (1966)].

The oxiranes (epoxyalcohols) as preferred compounds of the general formula (V) where X and Y=O and Z=H are prepared, for example, from the corresponding allyl alcohols by enantioselective epoxidation (see Pfenninger, "Asymmetric Epoxidation of Allylic Alcohols: The Skarplen Epoxidation" in Synthesis 1986, pp. 89–116). They are then employed as such (Z=H) or alternatively converted into the corresponding tosylates (Z=SO$_2$C$_6$H$_4$CH$_3$) by standard methods, for example by reaction with 4-toluenesulfonyl chloride; and an analogous situation applies to the other nucleofugic groups mentioned.

A further embodiment of the invention is a twistable liquid-crystal phase containing at least one chiral compound, the chiral compound contained being at least one compound of the general formula (I). The term "twistable liquid-crystal phase" is taken to mean nematic, cholesteric or tilted smectic, in particular, SmC phases.

The twistable liquid-crystal phases comprise 2 to 20, preferably 2 to 15 components, including at least one of the chiral compounds claimed according to the invention. The other components are preferably selected from the group comprising the known compounds, having nematic, cholesteric and/or tilted smectic phases, including, for example, Schiff bases, biphenyls, terphenyls, phenylcyclohexanes, cyclohexylbiphenyls, pyrimidines, cinnamates, cholesterol esters and various bridged, multinuclear esters of p-alkylbenzoic acids with polar terminal groups.

In general, even before addition of the chiral compound, the commercially available liquid-crystal phases exist as mixtures of a very wide variety of components of which at least one is mesogenic, i.e. as compound, in derivatized form or mixed with certain co-components exhibits of liquid-crystal phase [=at least one enantiotropic (clear point>melting point) or mono-tropic (clear point<melting point) mesophase formation can be expected].

In particular, the twistable liquid-crystal phase contains a phenyl pyrimidine compound having a S$_c$ phase, for example a 4-(5-alkyl-pyrimidin-2-yl)-1-alkoxybenzene, besides at least one of the chiral compounds claimed according to the invention.

The liquid-crystal phases generally contain 0.01 to 70% by weight, in particular 0.05 to 50% by weight, of the compound(s) according to the invention.

The compounds according to the invention are suitable, in particular, as dopes for tilted smectic liquid-crystal phases, since they convert the latter into ferroelectric liquid-crystal phases; the values for spontaneous polarization (P$_s$) are in the range from about 30 to 70 nC.cm$^{-2}$ (extrapolated to the pure compound).

EXAMPLES

Preparation Examples 1 to 8

(2S,3S)-(−)-2-[4-(5-octylpyrimidin-2-yl)phenyloxy]-methyl-3-propyl-oxirane (Example 1).

0.16 g of NaH (5 mmol), as an 80% strength dispersion in oil, is added to a solution of 1.42 g (5 mmol) of 2-(4-hydroxyphenyl)-5-n-octylpyrimidine in 50 ml of dimethylformamide at a temperature of 0° C. When the evolution of gas has subsided, 1.35 g (7 mmol) of (2S, 3S)-1-mesyloxy-2,3-epoxyhexane are added, and the mixture is stirred for 6 hours at 0° C. The mixture is subsequently hydrolized in 100 ml of ice water and extracted with dichloromethane. After three-fold column chromatography (silica gel, dichloromethane), 0.61 g (32% of theory) of colorless crystals are obtained. The IR spectrum (in KBr) and the $^1$H NMR spectrum (in CDCl$_3$) support the structural formula indicated, and the optical rotation is ($\alpha$) $_D^{25}$: −18.8° (c=10, CH$_2$Cl$_2$).

When the corresponding phenol (II), (III) or (IV) and the epoxyalcohols (V) are employed, this procedure and the one below are representative of all compounds in table (I) below.

(2S,3S)-(−)-2-[4-(5-nonyl-pyrimidin-2-yl)phenyloxy]-methyl-3-pentyl-oxirane (Example 4).

1.31 g (5 mmol) of triphenyl phosphine and 0.79 g (5 mmol) of diethyl azodicarboxylate are combined in 10 ml of tetrahydrofuran at 0° C. After 20 minutes, 1.49 g (5 mmol) of 2-(4-hydroxyphenyl)-5-n-nonylpyrimidine and 0.72 g (5 mmol) of (2S,3S)-2,3-epoxyoctane, each in 8 ml of tetrahydrofuran, are added. After 24 hours, the mixture is evaporated to dryness in vacuo, and the residue is chromatographed on silica gel (200 g) using CH$_2$Cl$_2$. After recrystallization from hexane, 0.79 g of colorless crystals is obtained; ($\alpha$) $_D^{25}$: −15.3° (c=5,CHCl$_3$)

TABLE I

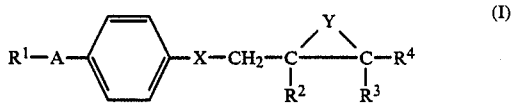

(X and Y = O; $R^2$ and $R^3$ = H)

| Ex. No. | A | $R^1$ | $R^4$ | Phase Sequence* (°C.) C | $S_B$ | $S_A$ | I |
|---|---|---|---|---|---|---|---|
| 1 | 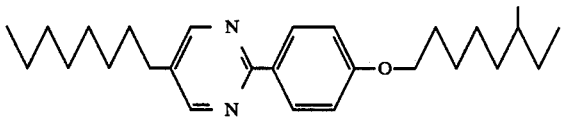 | $H_{17}C_8$ | $C_3H_7$ | · 90 | — | — | · |
| 2 | " | $H_{17}C_8$ | $C_4H_9$ | · 98 | — | — | · |
| 3 | " | $H_{17}C_8$ | $C_5H_{11}$ | · 106 | — | — | · |
| 4 | " | $H_{19}C_9$ | $C_5H_{11}$ | · 104 | — | — | · |
| 5 | " | $H_{21}C_{10}$ | $C_3H_7$ | · 88 | — | — | · |
| 6 | " | $H_{21}C_{10}$ | $C_7H_{15}$ | · 107 | — | — | · |
| 7 | 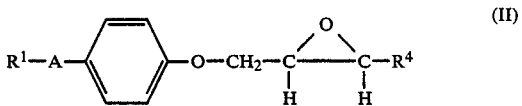 | $H_{17}C_8$ | $C_3H_7$ | · 55 | · 90 | · 102 | · |
| 8 | " | $H_{17}C_8$ | $C_5H_{11}$ | · 70 | · 101 | · 104 | · a |

*C = crystalline, S = smectic, I = isotropic
a $S_F$ must replace $S_B$ in this case.

Use Examples 1 to 8

In order to test the activity of the compounds described above as dopes in liquid-crystal systems, they are mixed, in concentrations of in each case 10 mol% (or in one case 25 mol%), with the racemate of the compound 4-(5-octylpyrimidin-2-yl)-1-(6-methyloct-1-oxy)benzene, and the values for spontaneous polarization ($P_s$ in nC.cm$^{-2}$), for the switching time $\tau$ (in μs) and for the optical tilt angle of the SmC* phase θ (in °) of the mixture are determined in each case.

The $P_s$ values are measured by the method of Sawyer et al. (Phys. Rev. 35, 269 to 273, 1930), in which a special measuring cell [Skarp et al. in Ferroelectric Letters Vol. 06, 000 (1986)] is used in which the $\tau$- and θ-values are also determined. At a cell path length of 2 μm, a uniform planar orientation of the liquid crystals in the SmC* phase is achieved through shearing [SSFLC technique, Clark et al., Appl. Phys. Lett. 36, 889 (1980)]. After placing the measuring cell between two crossed polarizers, the switching time is determined using a photodiode and the optical tilt angle or the switching angle is determined by rotating the measuring cell from maximum to minimum light passage through the measurement arrangement. Table II summarizes the results for the mixtures. Besides the values for Ps,$\tau$ and 2θ (in each case at 25° C.), the SmC* range for the particular mixture is specified; the values in parentheses here indicate the supercoolable lower temperature limit of the SmC* phase.

TABLE II

| Compound Ex. No. | Proportion of the Compound in mol % | $S_c$* phase of the mixture (°C.) | $P_s$ | $\tau$ | 2θ |
|---|---|---|---|---|---|
| 1 | 10 | 7 to 51 (5) | +4.3 | 215 | 48 |
| 1 | 25 | 7 to 51 (5) | +13.2 | 55 | 48 |
| 2 | 10 | 14 to 55 (2) | +5.5 | 85 | 46 |
| 3 | 10 | 5 to 54 (2) | +6.1 | 98 | 50 |
| 4 | 10 | 8 to 53 (3) | +5.6 | 100 | 58 |
| 5 | 10 | 12 to 51 (4) | +3.8 | 100 | 42 |
| 6 | 10 | 13 to 53 (−) | +5.8 | 285 | 52 |
| 7 | 10 | 12 to 45 (2) | +2.7 | 220 | 38 |
| 8 | 10 | 18 to 51 (5) | +3.1 | 106 | 39 |

Phase sequence of the basic component of the mixture: c 13.1 $S_c$ 49.3 $S_A$ 58.9 I (2.5)

We claim:

1. A chiral compound of the formula (I)

$$R^1-A-\underset{}{\bigodot}-X-CH_2-\underset{R^2}{\overset{Y}{\underset{|}{C}}}-\underset{R^3}{\overset{|}{C}}-R^4 \quad (I)$$

wherein
$R^1$ is straight-chain or branched ($C_1$-$C_{12}$) alkyl, where one or two non-neighboring $CH_2$ groups may be replaced by O and/or S atoms,
A is diazine-2,5-diyl or diazine-3,6-diyl,
X and Y are O and/or S, and
$R^2$, $R^3$ and $R^4$, independently of one another are H, straight-chain ($C_1$-$C_{10}$)alkyl or branched ($C_3$-$C_{10}$)alkyl, where $R^2$, $R^3$ and $R^4$ are not simultaneously H.

2. A chiral compound as claimed in claim 1, wherein A is pyrimidine-2,5-diyl.

3. A chiral compound of the formula (II)

$$R^1-A-\underset{}{\bigodot}-O-CH_2-\underset{H}{\overset{O}{\underset{|}{C}}}-\underset{H}{\overset{|}{C}}-R^4 \quad (II)$$

wherein $R^1$ is straight-chain ($C_5$-$C_{11}$) alkyl, where a $CH_2$ group may be replaced by an O or S atom, A is diazine-2,5-diyl or diazine-3,6-diyl, and $R_4$ is straight-chain or branched ($C_3$-$C_7$) alkyl.

4. A chiral compound as claimed in claim 3, wherein A is pyrimidine-2,5-diyl.

5. A twistable liquid-crystal mixture comprising at least one chiral compound of the formula (I) as claimed in claim 1 and a compound having nematic, cholesteric or tilted smectic phases.

6. A twistable liquid-crystal mixture comprising at least one chiral compound of the formula (I) as claimed in claim 1 and a phenyl pyrimidine compound having a $S_c$ phase.

7. A liquid-crystal display element containing a twistable liquid-crystal mixture comprising at least one chiral compound of the formula (I) as claimed in claim 1.

8. A twistable liquid-crystal mixture comprising at least one chiral compound of the formula (II) as claimed in claim 3 and a compound having nematic, cholesteric or tilted smectic phases.

9. A twistable liquid-crystal mixture comprising at least one chiral compound of the formula (II) as claimed in claim 3 and a phenyl pyrimidine compound having a $S_c$ phase.

10. A liquid-crystal display element containing a twistable liquid-crystal mixture comprising at least one chiral compound of the formula (II) as claimed in claim 3.

* * * * *